US008216823B2

(12) United States Patent
Finn

(10) Patent No.: US 8,216,823 B2
(45) Date of Patent: Jul. 10, 2012

(54) TRANSPORT MEDIA

(75) Inventor: Susan J. Finn, Bolton (CA)

(73) Assignee: Starplex Scientific Inc., Etobicoke, Ontario (CA)

(*) Notice: Subject to any disclaimer, the term of this patent is extended or adjusted under 35 U.S.C. 154(b) by 993 days.

(21) Appl. No.: 12/152,343

(22) Filed: May 14, 2008

(65) Prior Publication Data

US 2009/0047729 A1 Feb. 19, 2009

Related U.S. Application Data

(60) Provisional application No. 60/938,746, filed on May 18, 2007.

(51) Int. Cl.
*C12N 1/20* (2006.01)

(52) U.S. Cl. ................................... 435/253.6

(58) Field of Classification Search .......... None
See application file for complete search history.

(56) References Cited

OTHER PUBLICATIONS http://www.quebact.com/index.php/en/support/technical-data/23-1251, Jan. 5, 1998, accesses Aug. 23, 2011. (B.C.Y.E.(A-Buffered Charcoal Yeast Extract) Agar).*
The Oxoid Manual, 9th Edition 2006, Compiled by E. Y. Bridson, pp. 80 and 93.*
Feeley et al., Journal of Clinical Microbiology, Oct. 1979, p. 437-441.*

* cited by examiner

*Primary Examiner* — Irene Marx
(74) *Attorney, Agent, or Firm* — Wood, Phillips, Katz, Clark & Mortimer

(57) ABSTRACT

A transport media, particularly for fastidious microorganisms, has a concentration of activated charcoal less than 10 grams per liter of water. This maintains viability of the microorganisms while permitting Gram interpretation of the specimen.

1 Claim, No Drawings

TRANSPORT MEDIA

FIELD OF THE INVENTION

The present invention relates to media for transporting microorganisms.

BACKGROUND

Maintaining the viability of clinically relevant pathogens for subsequent diagnosis is a major concern in the healthcare field, especially in outpatient settings where delay in transit may be expected, and specialized transport media is utilized for this purpose.

The use of transport media was first popularized in the 1940's, when Robert Stuart, a public health microbiologist in Glasgow, Scotland, developed and disclosed to the world a transport medium consisting of sodium glycerophosphate, sodium thioglycollate, methylene blue, agar and calcium chloride. The Stuart media was subsequently improved by C. R. Amies, of the Ontario Public Health Laboratory, who substituted an inorganic phosphate buffer for the glycerophosphate of the Stuart media, and added sodium, calcium and magnesium salts. Both the Stuart and Amies media remain widely used for transporting a wide variety of microorganisms.

For fastidious organisms such as *Heomophilus influenza, Neisseria gonorrhoeae* and *Streptococcus pneuemoniae*, activated charcoal at the rate of 10 g per liter of water is ubiquitously added to the media, as neither the Stuart nor Amies media provide satisfactory conditions for maintaining viability otherwise. The charcoal is believed to remove toxic substances often found in the specimens, prevent photochemical oxidation reactions, reduce production of potentially toxic hydrogen peroxide and trap free radicals. However, the presence of charcoal particles can interfere with the Gram interpretation of the specimen. Charcoal particles in the smear can mask or even be confused with Gram positive organisms. Since Gram stains are often the initial result available to physicians, this has a significant impact on patient management. Accordingly, it is commonplace for transport media to be maintained in clinical inventory in both charcoal-containing and charcoal-absent variants.

SUMMARY OF THE INVENTION

The present invention pertains to a transport media which has a charcoal concentration sufficiently low to permit Gram interpretation yet maintains the viability of fastidious microorganisms. This permits a single inventory to be maintained, with commensurate impacts on cost and convenience.

DETAILED DESCRIPTION

To prepare transport media according to the invention, various ingredients are solubilized in water. In an exemplary embodiment, components as listed below are suspended in 1.0 liters of distilled water; heated to boiling with frequent agitation to solubilize the ingredients; dispensed into screw-capped tubes; and sterilized at 121° C. for 15 minutes.

| | |
|---|---|
| Activated charcoal | 0.50 grams |
| MOPS Acid | 3.15 grams |
| MOPS Salt | 8.48 grams |
| Potassium Chloride | 1.00 grams |
| Calcium Chloride | 1.26 grams |
| Magnesium Chloride | 5.48 grams |
| Sodium Thiosulfate | 10.90 grams |
| N-Acetyl Glucosamine | 0.50 grams |
| Betaine | 5.00 grams |
| Gluten Hydrolysate from maize | 0.50 grams |
| Agar | 7.50 grams |

The media was tested in accordance with the procedures set forth in *Quality Control of Microbiological Transport Systems; Approved Standard*, CLSI, (formerly NCCLS) M-40A. Strains included *Neisseria gonorrhoeae* (NG), *Haemophilus influenzae* (HI), *Streptococcus pneumoniae* (SPN), *Streptococcus pyogenes* (SP), *P. aeruginosa* (PA) and *S. aureus* (SA) and *E. coli* (EC). Swabs inoculated with NG, HI, SPN were held at 4° C. and those inoculated with SP, PA, SA, and EC were held at room temperature (RT). Organism survival was evaluated by determining CFU/ml at 0, 6, 24 and 48 hours by plating 100 ul of the suspension to appropriate aerobic media. Dilutions with visible growth at 48 hours incubation with a range of 30-300 CFU were evaluated. Combinations were tested in triplicate and compared using a two-tailed student t-Test. For the Gram stain, both swabs were inoculated with 0.5 McFarland suspensions of each strain and held for ½ hour at RT prior to preparing and staining. The results of the testing are set forth below.

| | Initial Count | % Recovery Storage Time/Conditions | | | |
|---|---|---|---|---|---|
| Test Organism | | 24RT | 24REF | 48RT | 48REF |
| *Haemophilus influenzae* ATCC 10211 | 330 | 31 | 34 | 19 | 18 |
| *Neisseria gonorrhoeae* ATCC 43069 | 428 | 0 | 11 | ND | ND |
| *Streptococcus pneumoniae* ATCC 6305 | 298 | ND | ND | 11 | 18 |
| *Streptococcus pyogenes* ATCC 19615 | 92 | ND | ND | 70 | 86 |
| *Propionibacterium acnes* ATCC 6919 | 222 | ND | ND | 39 | 43 |
| *Prevotella melaninogenica* ATCC 25845 | 314 | 0 | 48 | 0 | 7 |
| *Bacteroides fragilis* ATCC 25285 | 276 | ND | ND | 93 | 84 |
| *Peptostreptococcus anaerobius* ATCC 27337 | 205 | 7 | 40 | 1 | 14 |

24RT = 24 hours room temperature storage
24REF = 24 hours refrigerated storage
48RT = 48 hours room temperature storage
48REF = 48 hours refrigerated storage
ND = no data A second series of tests was carried out, with the charcoal amount varied to 1.0 grams per liter, the results of which being as follows:

| Test Organism | Initial Count | % Recovery Storage Time/Conditions | | | |
|---|---|---|---|---|---|
| | | 24RT | 24REF | 48RT | 48REF |
| *Haemophilus influenzae* ATCC 10211 | 204 | 25 | 30 | 12 | 15 |
| *Neisseria gonorrhoeae* ATCC 43069 | 412 | 0 | 19 | ND | ND |
| *Streptococcus pneumoniae* ATCC 6305 | 172 | ND | ND | 10 | 27 |
| *Streptococcus pyogenes* ATCC 19615 | 36 | ND | ND | 39 | 76 |
| *Propionibacterium acnes* ATCC 6919 | 319 | ND | ND | 63 | 44 |
| *Prevotella melaninogenica* ATCC 25845 | 827 | 0 | 83 | 0 | 12 |
| *Bacteroides fragilis* ATCC 25285 | 333 | ND | ND | 59 | 88 |
| *Peptostreptococcus anaerobius* ATCC 27337 | 782 | 3 | 39 | 0 | 26 |

In both tests, because of the relatively low charcoal concentration, Gram, interpretation of the samples was possible. Surprisingly, in view of the relatively low charcoal concentrations, under refrigerated conditions, the various microorganisms remained viable at levels deemed useful according to CLSI M-40A.

A third series of tests was carried out, comparing the exemplary transport media with the charcoal amounts varied to 1.0 grams and 0.5 grams for both ATCC and clinical strains.

The results of such testing for both the ATCC and clinical strains are set forth below.

The 0.5 g/l and 1.0 g/l embodiments therefore each constitute a transport medium which has a charcoal concentration sufficiently low to permit Gram interpretation yet maintains the viability of fastidious microorganisms. This permits a single inventory to be maintained, with commensurate impacts on cost and convenience.

Whereas but two embodiments of the invention are herein described, various modifications thereto are contemplated.

For example, whereas specific ingredients are listed, other analogues could be substituted therefore. For example, buffers other than MOPS acid and salt could be utilized. As well, osmolarity can be maintained otherwise than via Betaine, and salts other than NaCl, KCl and MgCl could be utilized for

| Test Organism | Storage Conditions | Charcoal amount varied to 1.0 grams Storage Time (hrs.) | | | Charcoal amount varied to 0.5 grams Storage Time (hrs.) | | |
|---|---|---|---|---|---|---|---|
| | | 6 | 24 | 48 | 6 | 24 | 48 |
| | | % Viability compared to Baseline for ATCC strains | | | | | |
| *S. pyogenes* ATCC 19615 | RT | 53 | 34 | 15 | 86 | 55 | 52 |
| *S. pneumoniae* ATCC 6305 | Refrigerated | 80 | 93 | 74 | 64 | 64 | 10 |
| *P. aeruginosa* ATCC 27853 | RT | 82 | TNTC | TNTC | 143 | TNTC | TNTC |
| *S. aureus* ATCC 25923 | RT | 104 | 67 | 40 | 72 | 85 | 88 |
| *E. coli* ATCC 25922 | RT | 110 | TNTC | TNTC | 211 | TNTC | TNTC |
| *N. gonorrhoeae* ATCC 49221 | Refrigerated | 61 | 2 | 1 | 13 | 34 | 1 |
| *H. influenzae* ATCC 10211 | Refrigerated | 90 | 59 | 12 | 56 | 33 | 53 |
| | | % Viability compared to Baseline for clinical strains | | | | | |
| *S. pyogenes* | RT | 195 | 31 | 13 | 53 | 34 | 31 |
| *S. pneumoniae* | Refrigerated | 71 | 74 | 13 | 140 | 103 | 34 |
| *P. aeruginosa* | RT | 40 | TNTC | TNTC | 61 | TNTC | TNTC |
| *S. aureus* | RT | 38 | 21 | 12 | 135 | 264 | 348 |
| *E. coli* | RT | 259 | TNTC | TNTC | TNTC | TNTC | TNTC |
| *N. gonorrhoeae* | Refrigerated | 20 | 3 | 0 | 67 | 5 | 0 |
| *H. influenzae* | Refrigerated | 52 | 17 | 17 | 54 | 15 | 5 |

TNTC = too numerous to count

In the third series of tests, there was again a significant reduction in particles with improved visualization of organisms and background staining and except for *Streptococcus pneumoniae*, there was no statistical difference in the ability of the two media to maintain the viability of the clinical and ATCC isolates. The discrepancy in viable counts observed for *S. pneumoniae* in the third series of tests is likely a reflection of the fastidious nature of the organisms or variability in the colony counts and not a result of the reduced charcoal in the media.

permeability control. Further, the various components could be provided in varying amounts.

Accordingly, the invention should be understood as limited only by the accompanying claims, purposively construed.

The invention claimed is:

1. An improved aqueous transport medium of the type capable of maintaining the viability of fastidious microorganisms, the transport medium consisting essentially of:

| | |
|---|---:|
| Water | 1.0 liters |
| Activated charcoal | 1.0 grams |
| and, in solution | |
| MOPS | 3.15 grams |
| MOPS Sodium Salt | 8.48 grams |
| Potassium Chloride | 1.00 grams |
| Calcium Chloride | 1.26 grams |
| Magnesium Chloride | 5.48 grams |
| Sodium Thiosulfate | 10.90 grams |
| N-Acetyl Glucosamine | 0.50 grams |
| Betaine | 5.00 grams |
| Gluten Hydrolysate from maize | 0.50 grams |
| Agar | 7.50 grams. |

\* \* \* \* \*